United States Patent [19]
Schüpbach et al.

[11] Patent Number: 5,556,745
[45] Date of Patent: Sep. 17, 1996

[54] METHOD FOR THE DETECTION AND QUANTITATIVE DETERMINATION OF ANTIGEN IN A TEST SAMPLE CONTAINING IMMUNE COMPLEXES OF ANTIGEN BOUND TO ANTIBODIES AND TO RHEUMATOID FACTORS

[76] Inventors: Jörg Schüpbach, Bachtalsteig 4, CH-5400 Ennetbaden; Jürg Böni, Kollerstrasse 8, CH-5430 Wettingen, both of Switzerland

[21] Appl. No.: 253,297

[22] Filed: Jun. 3, 1994

[51] Int. Cl.$^6$ .................................. C12Q 1/00
[52] U.S. Cl. .................. 435/5; 435/7.1; 435/7.2; 435/7.22; 435/7.31; 435/7.32; 435/7.33; 435/7.34; 435/7.35; 435/961; 435/962; 435/974; 436/509
[58] Field of Search .................. 435/4, 7.1, 7.2, 435/7.22, 7.31, 7.32, 7.33–7.35, 961, 962, 974; 436/509

[56] References Cited

U.S. PATENT DOCUMENTS 4,900,684  2/1990  Hansen .................................. 436/518

OTHER PUBLICATIONS

Kageyama et al, "An improved method for the detection of HIV antigen in the blood of carriers", *Journal of Virological Methods*, vol. 22, No. 2–3, pp. 125–131, 1988.

Schechter et al, "Heat Versus Acid Dissociation of Immune Complexes for the Detection of p. 24 Antigenemia", *International Conference on AIDS*, vol. 10, No. 1, (Abstract No. PB0089), p. 166, 7–12 Aug. 1994.

Kestens, et al, "HIV–Antigen Detection in Immune Complexes and Its Relation to the Clinical and Immunological Status", *International Conference on AIDS*, vol. 6, No. 2, (Abstract No. F.A. 356), p. 165, 22 Jun. 1990.

de Wolf, et al, "Risk of AIDS related complex and AIDS in homosexual men with persistent HIV antigenaemia", *British Medical Journal* (1987) 295: 569–572.

Court Pedersen et al, "Temporal relation of antigenaemia and loss of antibodies to core antigens to development of clinical disease in HIV infection", *British Medical Journal* (1987) 295:567–569.

Joep M. A. Lange et al, "Viral Gene Expression, Antibody Production and Immune Complex Formation in Human Immunodeficiency Virus Infection", *AIDS* (1987), 1:15–20.

Parunag Nishanian et al, "A Simple Method for Improved Assay Demonstrates that HIV p24 Antigen is Present as Immune Complexes in Most Sera from HIV–Infected Individuals", *J. Infectious Diseases* (1990) 162:21–28.

Steven A. Miles et al, "Rapid Serologic Testing with Immune–Complex–Dissociated HIV p24 Antigen for Early Detection of HIV Infection in Neonates", *The New England Journal of Medicine* (1993) 328:297–302, No. 5.

Jörg Schüpbach et al, "Quantitative and sensitive detection of immune–complexed and free HIV antigen after boiling of serum", *Journal of Virological Methods* (1993) 43:247–256.

Mario Portera et al, "Free and Antibody–Complexed Antigen and Antibody Profile in Apparently Healthy HIV Seropositive Individuals and in AIDS Patients", *Journal of Medical Virology* (1990) 30:30–35.

Lin Qi Zhang et al, "Detection, quantification and sequencing of HIV–1 from the plasma of seropositive individuals and from factor VIII concentrates", *AIDS* (1991) 5:675–681.

Jörg Schüpbach et al, "Antibodies to HTLV–III in Swiss Patients with AIDS and Pre–AIDS and in Groups at Risk for AIDS", *The New England Journal of Medicine* (1985) 312:265–270.

Jonathan N. Weber et al, "Human Immunodeficiency Virus Infection in Two Cohorts of Homosexual Men: Neutralising Sera and Association of Anti–Gag Antibody with Prognosis" *The Lancet* (Jan. 17, 1987) pp. 119–122.

Joep M. A. Lange et al, "Persistent HIV antigenaemia and decline of HIV core antibodies associated with transition to AIDS", *British Medical Journal* (1986) 293:1459–1462.

*Primary Examiner*—Christine M. Nucker
*Assistant Examiner*—Jeffrey Stucker
*Attorney, Agent, or Firm*—Burns, Doane, Swecker & Mathis

[57] ABSTRACT

The invention is a simple and rapid method for immune complex dissociation and destruction of rheumatoid factors. It permits the quantitative measurement of the total, i.e., free and immune complex-bound, antigen contained in a test sample. The method involves heating the test sample to a point sufficiently above 65° C. at which the antigen-binding function of antibodies is destroyed. As a consequence, interference by rheumatoid factors is eliminated and the antigen is released from immune complexes, after which it can be measured in an antigen assay that recognizes the heat-denatured antigen.

11 Claims, 5 Drawing Sheets

METHOD FOR THE DETECTION AND QUANTITATIVE DETERMINATION OF ANTIGEN IN A TEST SAMPLE CONTAINING IMMUNE COMPLEXES OF ANTIGEN BOUND TO ANTIBODIES AND TO RHEUMATOID FACTORS

BACKGROUND OF THE INVENTION

Antigen (Ag) assays are of increasing importance as diagnostic tools, e.g., for the diagnosis of infectious diseases in humans or animals. In addition, quantitative measurement of Ag is useful for the follow-up of infected individuals. In viral infections, for example, the determination of the viral load is important with respect to prognosis, indication for antiviral treatment, or assessment of treatment success. Unfortunately, in the presence of antibody (Ab) the Ag becomes bound in immune complexes (IC). Such complexed Ag is no longer freely available to binding to the immune reagents used in antigen assays, i.e., detection by such assays, as demonstrated in the case of infection with the human immunodeficiency virus, HIV (de Wolf et al., *Br. Med. J.*, 295:569–572, 1987; Pedersen et al., *Br. Med. J.*, 295:567–569, 1987; Lange et al., *AIDS*, 1:15–20, 1987). Several groups have developed IC dissociation procedures based on either treatment with acids (for an example see Lange et al., *AIDS*, 1:15–20, 1987) or bases. While these procedures lead to a significantly higher detection rate of antigenemia (Nishanian et al., *J. Inf. Dis.*, 162:21–28, 1990; Miles et al., *N. Engl. J. Med.*, 328:297–302 1992), convincing data showing that they are capable of freeing all IC-bound Ag, thus making possible a truly quantitative measurement, have not been presented.

Another problem that impairs the quality of Ag assays is the presence of rheumatoid factors (RF) in a test sample, i.e., of antibodies that have specificity for immunoglobulins. Such rheumatoid factors may link the capture and tracer antibodies used in an Ag assay, thereby leading to overestimation of Ag concentrations or outright false-positive results. The usual way to deal with rheumatoid factors is their preabsorption with high concentrations of immunoglobulin. However, this does not represent a safe remedy, and its effect cannot be readily controlled.

SUMMARY AND OBJECTS OF THE INVENTION

It is an object of the invention to propose a simple method permitting the detection and quantification of an Ag in a test sample by an Ag assay even if a fraction or the whole of said Ag is bound in IC.

It is a further object of the invention to provide a method for destroying rheumatoid factors, thereby eliminating this source of imprecision and increasing the specificity and precision of antigen assays.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE FIGURES

FIG. 1 illustrates the effect of heat denaturation upon the detection of HIV antigen in artificial immune complexes, and the effect of IC dissociation methods on IC of varying antibody/Ag ratio. Model IC were formed by overnight incubation of HIV-positive serum admixed to a constant volume of HIV-negative serum and a constant amount of exogenous HIV Ag.

FIG. 1A: Effect of heat denaturation on the detection of a constant amount of exogenous Ag admixed to HIV-positive (P1P3) or HIV-negative (N4-N6) sera. ▨, undenatured; ■, heat-denatured. FIG. 1B: Representative standard curves prepared with duplicates of undenatured (□), heat-denatured (■), or acid-denatured (▲) Ag standards diluted in serum-free buffer. FIG. 1C: Representative standard curves prepared with duplicates of heat-denatured Ag diluted in serum-free buffer (■), HIV-positive human sera (♦), HIV-negative human sera (◊). The flattening of the curves towards the lower concentrations of exogenous Ag is due to the presence of endogenous Ag in HIV-positive sera. FIG. 1D: Standard curves as in FIG. 1C and with the same symbols, but after subtraction of the individual background absorbance values (i.e., the zero absorbances of FIG. 1C). The curves are parallel to each other over most of the Ag concentration range. The remaining irregularities (flattening or steeper slopes) at the lower end of the concentration range are due to imprecision of measurement and the use of a logarithmic scale.

FIG. 3 demonstrates that heat denaturation is superior to acidification with respect to detecting HIV antigen in clinical samples, and shows the comparison of Ag detection in HIV-negative or -positive samples after different IC disruption procedures. The absorbance/cut-off value of an untreated (UD) sample is connected by a line with that obtained after heat denaturation (HD), and that after acid denaturation (AD). FIG. 3B, very strong reaction with p24; FIG. 3C, strong reaction; FIG. 3D, intermediate reaction; FIG. 3E, weak reaction; FIG. 3F, absence of reaction. Mean values and SD are indicated at the bottom of the figure.

DETAILED DESCRIPTION OF THE PREFERRED EMBODIMENTS

Figure 1A:
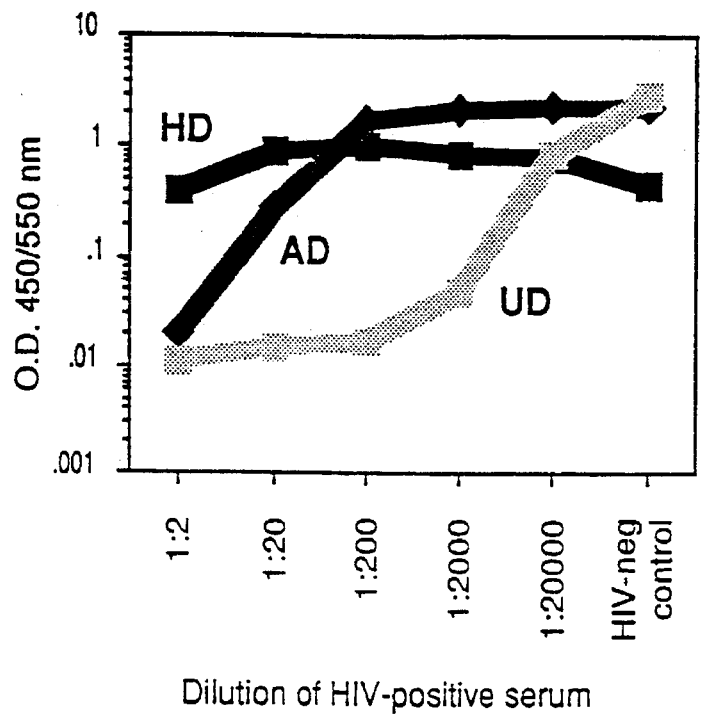
FIG. 1A: Comparison of Ag detected in undenatured (UD), acid-denatured (AD), and heat-denatured (HD) samples.

The following are definitions of terms and phrases as used herein:

The term "antigen (Ag)" is a substance that can induce a detectable immune response when introduced into an animal or into man.

The phrase "antigen tests/assays" refers to any test or assay that detects and identifies Ag by a method which requires the specific binding of Ag to Ab or to other reagent(s) that exhibit(s) such Ag-specific binding properties.

The phrase "immune complexes (IC)" refers to Ag-antibody (Ab) complexes formed when Ab is added to Ag, according to the fundamental law of immunology, Ag+Ab->Ag–Ab.

The phrase "immune complex dissociation" refers to the method or process that leads to dissolution of IC, Ag–Ab–>Ag+Ab.

The phrase "rheumatoid factors (RF)" refers to any type of antibody that reacts with any kind of immunoglobulin.

The phrase "heat denaturation" refers to the heating of a test sample to a temperature above 65° C., thereby achieving at least the partial loss of Ag-binding function of Ab.

The phrase "capturing reagent" refers to Ab or other reagent used in an Ag assay, which captures the Ag present in a sample and immobilizes it, e.g., to the well of a microliter plate, a bead, or a particle.

The phrase "tracing reagent" refers to an Ab or other reagent used for the identification of captured Ag.

The proposed method involves destroying the Ag-binding function of the antibodies present in the sample by heat application, whereby the Ag is released from complexes and rendered amenable to quantitative detection by the Ag assay's immunological reagents, these reagents being capable of recognizing the Ag after such heating.

The following examples are presented in order to more fully illustrate the preferred embodiments of the invention. They should in no way be construed, however, as limiting the broad scope of the invention.

EXAMPLE 1

Quantitative and Sensitive Detection of Immune-complexed and Free HIV Antigen After Boiling of Serum The following Example is described in Schüpbach J. & Böni J; J. VIROL METHODS 1993; 43:247–256, which is hereby incorporated by reference in its entirety.

MATERIALS AND METHODS

Artificial HIV IC were formed by overnight incubation of HIV antibody-positive human serum with HIV culture supernatant. For IC disruption these samples or, alternatively, sera or plasma from HIV-positive patients or controls were diluted 1:3 with distilled water or a 0.5% solution of Triton X-100. The diluted samples were boiled in 1.5 ml Eppendorf tubes on a dry heat block (Techne DRI-BLOCK® DB-2A), or in a water bath, and assayed in duplicate by commercial HIV Ag detection kits from Du Pont de Nemours or Coulter. For comparison, Ag was also assayed without previous denaturation, or after acid disruption of immune complexes, using the Coulter Immune Complex Disruption (ICD) kit. Ag tests were performed according to the manufacturers' procedures, with the exception that the first incubation was for 2 hrs at room temperature on a microplate shaker.

RESULTS

The efficacy of various methods for immune complex dissociation was assessed in model systems using artificial complexes of HIV antigen and HIV-specific antibodies formed under controlled conditions. Pooled HIV-positive serum with a high titer of antibodies to p24, as assayed by Western blot, was serially diluted in antibody-negative serum and IC were formed by the addition of a constant amount of HIV Ag from supernatant of a HIV-positive cell culture to each serum dilution, resulting in a final concentration of added Ag of approximately 100 pg/ml. The samples were subjected to heat denaturation, acid treatment, or simple 3-fold dilution (to compensate for the dilution required in both IC disruption procedures) and assayed by the Coulter HIV-1 p24 Ag assay. FIG. 1A shows that heat denaturation yielded basically constant Ag concentrations in all samples, independent of the antibody/Ag ratio. In contrast, Ag concentrations obtained from both untreated or acid-treated samples were highly dependent on the antibody/Ag ratio and ranged from highly-positive to completely negative. The untreated HIV-positive serum had such a high concentration of p24-specific antibodies that a dilution of 1:2000 was sufficient to complex virtually all added Ag. Acid treatment yielded a quantitative recovery of Ag down to a dilution of 1:200. However, 90% of the added Ag remained undetectable at 1:20 and none was detectable at 1:2.

Figure 1B:
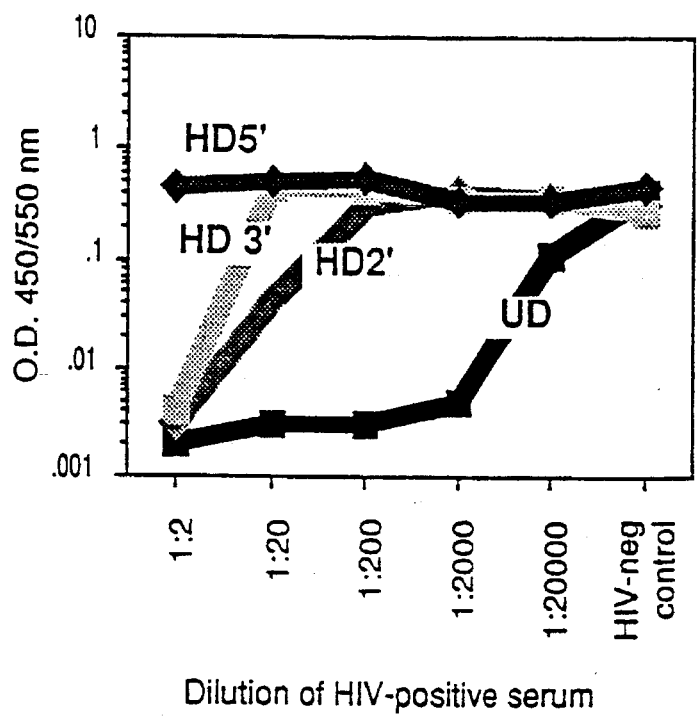
FIG. 1B: Effect of heat denaturation time (HD, in minutes) upon detection of complexed Ag.

FIG. 1B shows the effect of heat denaturation time on Ag detection. Denaturation at 100° C. for 2, 3, or 5 min was increasingly efficient in the release of complexed exogenous Ag. Denaturation for 2 min had an incomplete effect similar to that achieved by acid disrupture. Additional experiments showed unchanged good effect of denaturation for 6 or 7 min, but a slight decrease after 10 min (not shown). Temperatures of less than 100° C. were insufficient; 5 min/80° C. had no effect at all and 5 min/90° C. released only 5 to 10% of the input Ag (not shown).

Figure 2A:
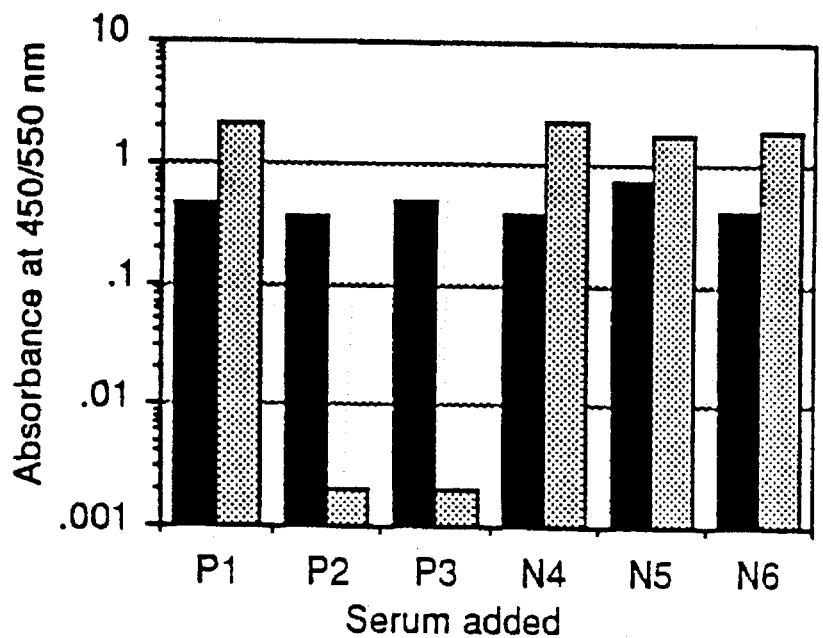
FIG. 2 shows that heat denaturation permits the quantitative recovery of HIV antigen independent of the presence and titer of antigen-specific antibodies.
Figure 2B:
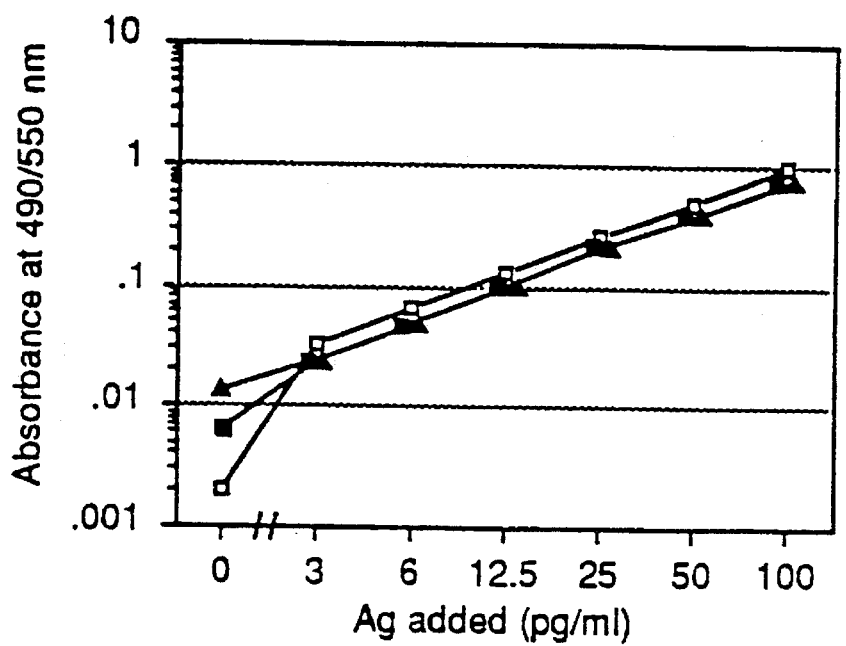
Figure 2C:
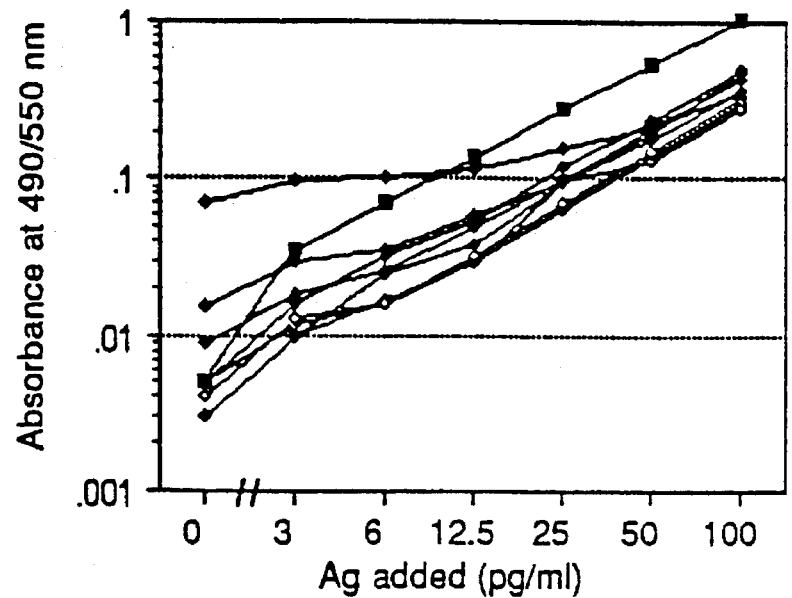
Figure 2D:
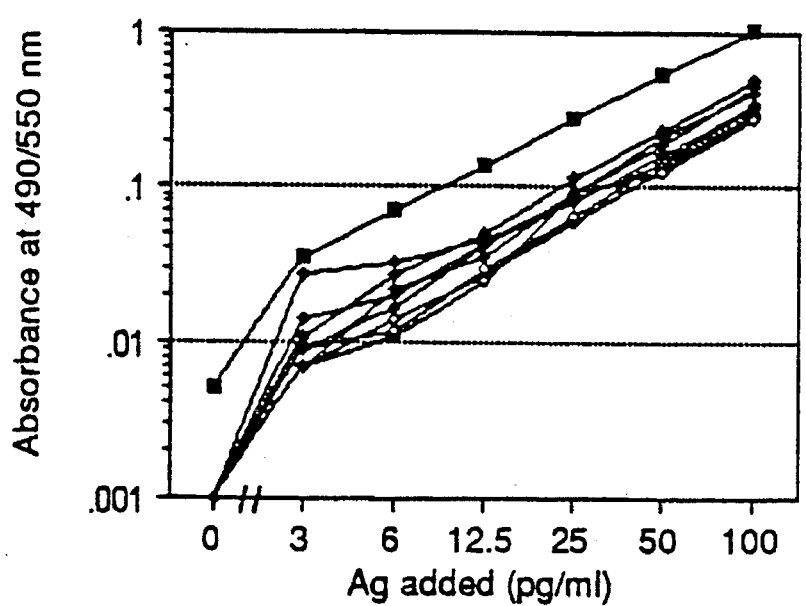

FIG. 2A shows the effect on the recognition of the same amount of exogenous Ag (in the order of 200 to 300 pg/ml) of adding to it each of 6 human sera and incubating overnight. Three of these sera (P1 to P3) were from HIV-positive patients and three (N4 to N6) from HIV-negative controls. No endogenous Ag was detected with or without previous heat denaturation in any of these samples (not shown). When mixed with the exogenous Ag results of Ag testing of the undenatured samples ranged from highly positive (absorbance 2,304) to completely negative. Western blot analysis for p24-specific antibodies revealed that serum P1 had only low reactivity, while P2 and P3 had medium and strong reactivity, respectively (not shown). Heat denaturation of the mixtures led to the detection of very similar amounts of Ag (mean absorbance 0.487, standard error 0.058) in all, independent of the presence and titer of antibodies to p24. Thus, although the absorbantes were significantly reduced, the variation was not different from that observed in those undenatured sera (P1,N4-N6) that permitted the detection of exogenous Ag (mean 2.076, standard error 0.102). Experiments with six additional antibody-negative plasma resulted in a mean absorbance of heat-denatured Ag that corresponded to 19%±3.2% of that of the undenatured sample (not shown). FIG. 2B shows that heat denaturation per se did not impair the recognition of Ag. Ag tests of Ag standards serially diluted from 100 to 3 pg/ml in serum-free buffer yielded the same absorbance values as undenatured or acid-denatured standards. When, however, the dilutions of Ag were made in HIV-positive or negative human serum, the resulting concentrations of heat-denatured Ag were reduced to about one-third (34%±3%) of those without serum; otherwise, the concentration curves had the same characteristics, i.e., they showed the same slope and did not vary by more than a factor of two from each other (FIGS. 2C, 2D).

Figure 3A:
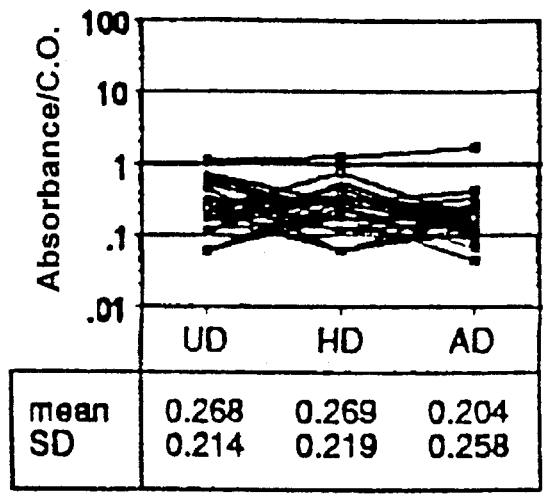
FIG. 3A shows the results of 38 HIV-negatives.
Figure 3B:
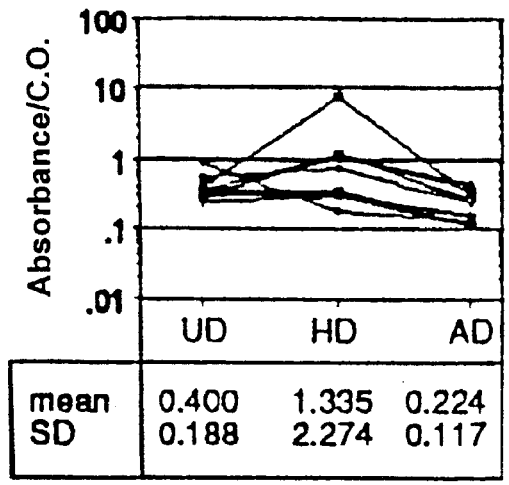
FIGS. 3B to 3F show each the results of 10 anti-HIV-positive sera that were ranged with respect to their anti-p24 antibody reaction as follows.
Figure 3C:
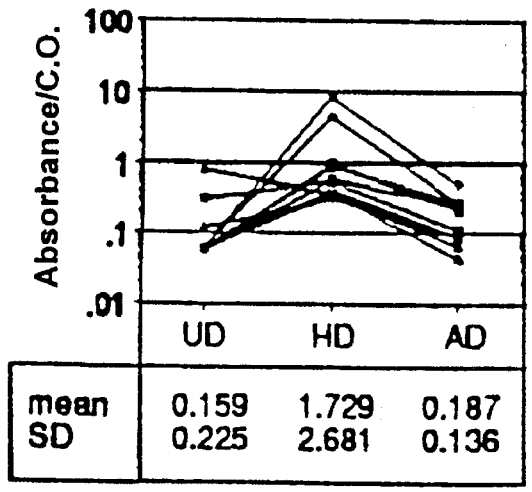
Figure 3D:
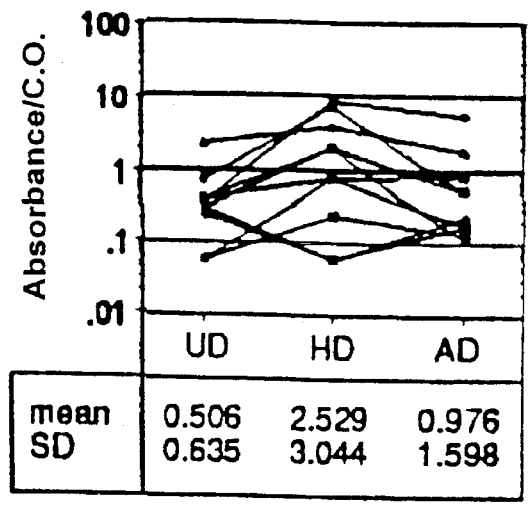
Figure 3E:
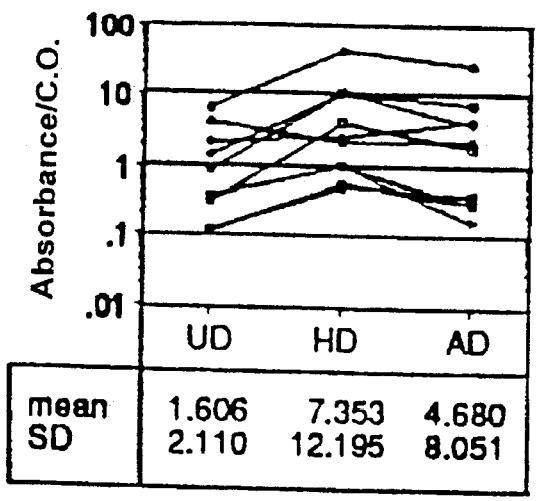

The efficacy of the various methods for immune complex dissociation was then assessed with samples from blood donors and HIV-infected patients, respectively. FIG. 3 shows Du Pont Ag test results with sera negative or positive for antibodies to HIV-1, as determined by enzyme immunoassay and Western blot. Similar results were found when some of the testing was done with Coulter kits (data not shown). FIG. 3A shows the results of 38 sera negative by Western blot tested undenatured, heat-denatured, or acid-denatured. Both undenatured and heat-denatured sera had a mean absorbance of 0.005 and a standard deviation (SD) of 0.004. Mean and SD were, with 0.009 and 0.012, resp., slightly but significantly different for acid-treated samples ($p \leq 0.006$, two-sided paired t-test). The cut-off (mean+3 SD) was set at 0.017 for both the untreated and heat-treated samples, while it was 0.045 for acidified samples. These values corresponded to 1.5 to 2 pg/ml for untreated, 4 to 5 pg/ml for heat-denatured, and 5 to 6 pg/ml for acid-denatured samples. One sample was consistently borderline to low-positive in all procedures; antigen neutralization could not be performed due to the lack of serum. FIGS. 3B to F show Ag detection in HIV-positive sera that were ranged into five groups of similar antibody reactivity to p24 by visual examination of Western blot strips, but were otherwise unselected. Clinical information on these patients is not available. Each of FIGS. 3A–F shows the results of 10 sera. All sera exhibiting very high (FIG. 3B) or high (FIG. 3C) anti-p24 titers were Ag-negative when tested undenatured or after acidification; heat denaturation, however, yielded 4 samples above cut-off in FIG. 3B and 3 in FIG. 3C. Neutralization assays confirmed the presence of Ag in all of the three sera whose absorbance/cut-off ratio was equal to or greater than 5.0 and in one serum that was just borderline.

Figure 3F:
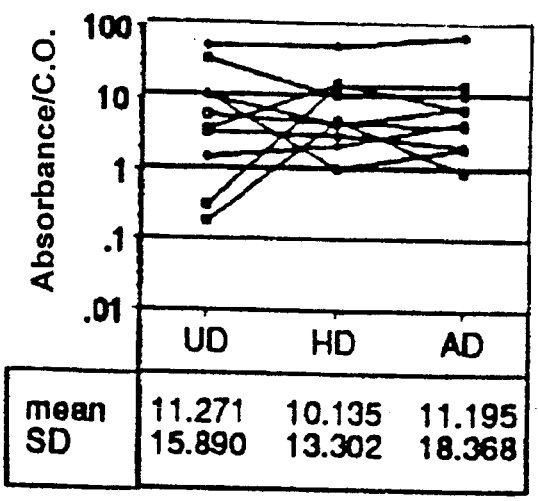

Neutralization was not successful in the three others. The effect of acidification increased with decreasing titer of p24 antibodies (FIG. 3D to F), but undenatured sera became also positive more frequently. Eight out of ten undenatured samples were above cut-off in the absence of anti-p24 antibodies (FIG. 3F). Statistics by $t$ test (two-sided, paired) indicated superiority of heat denaturation versus no treatment ($p \leq 0.004$) and versus acid denaturation ($p \leq 0.002$) in the 30 samples with the highest titers of anti-p24 antibodies (FIGS. B,C,D), while there were no significant differences for the 20 low-titered sera of FIGS. 3E and F.

Independent of whether the samples were tested denatured or undenatured, the mean absorbances were lowest in the patients with the highest antibody reaction to p24. The concentration of total Ag was reversely correlated with the titer of anti-p24 (FIGS. 3B to F).

The above results show that boiling of diluted serum or plasma samples releases IC-bound Ag. Heat denaturation permits a quantitative measurement of both IC-bound and free Ag present in serum (FIGS. 1A, 2A). The Ag release depends on time and temperature: 5 to 7 min/100° C. were sufficient (FIG. 1B). The use of heat-denatured standards permits quantification of the Ag despite the fact that absorbances are reduced in the presence of human serum (FIGS. 2B to D). The study of clinical samples showed that heat denaturation resulted in an increased presence and concentration of Ag among HIV antibody positives; this effect was most pronounced in individuals with high-titered antibody to p24 (FIG. 3).

Acidification of serum is currently the method of choice for the disrupture of IC. The data show, however, that acidification is not capable of detecting antigen present in concentrations as high as 100 pg/ml when antibodies to p24 are present at very high concentration (FIGS. 1A, 3). Others have found a two- to four-fold increase in the rate of Ag positivity after acidification. With the small selection of 50 HIV-positive samples investigated here, the effect of acidification was not significant (17 versus 13 positives; p=0.384; t-test). This discrepancy may be due to two factors: Firstly, the present samples were selected on the basis of anti-p24 antibody titers; this selection does not necessarily represent the clinical sample cohorts tested by others. However, in none of FIGS. 3A to F, which together represent the whole spectrum of HIV infection, did acid treatment result in a doubling of positivity (except in FIG. 3D where positivity doubled from one to two). Of more importance may be the fact that a low cut-off (mean+3 SD) was used for all testing independent of whether it was done with undenatured, acid-denatured, or heat-denatured samples. Others have used the manufacturer's cut-off (Nishanian et al., *J. Inf. Dis.*, 162:21–28, 1990), not specified it (Portera et al., *J. Med. Virol.*, 30:30–35, 1990), or have even used the manufacturer's cut-off for undenatured samples and a modified cut-off, e.g., mean+2 SD, for interpretation of acid-denatured samples (Miles et al., *N. Engl. J. Med.*, 328:297–302, 1992). Such interpretation is much in favor of the method that uses the mean+2 SD cutoff, since the cut-off of, e.g., the Du Pont Ag test is calculated by adding 0.080, i.e., 12 to 20 SD, to the mean of three negative controls.

The use of such a high cut-off in a population in which Ag positives are frequent is not reasonable. Thus, a much lower cut-off was chosen (mean+3 SD), which will result in one to two false-positives in a test population of 1000 Ag-negatives. These can be easily identified with the neutralization test which should be used consequently. Using this cut-off, the detection limit of the Du Pont Ag test with undenatured sera was 1.5 to 2 pg/ml, i.e., considerably lower than the 15±3 pg indicated for the same test but using undiluted serum (Nishanian et al., *J. Inf. Dis.*, 162:21–28, 1990). The use of the mean+3 SD cut-off instead of the mean +20 SD (corresponding to 8–16 pg/ml) increased the number of positive undenatured samples from 7 to 13 (FIG. 3). Had a cut-off corresponding to 10–20 pg/ml been chosen, acidification would indeed have resulted in at least a doubling of positives in FIGS. 3E and F. In FIG. 3F, e.g., only 2 to 4 of the undenatured, but 7 to 9 of the acid-denatured samples would have been positive and in FIG. 3E the number would have increased from 1 to 6. In this respect, our findings are in complete accordance with those of others.

The mean absorbance/cut-off ratio as well as the mean concentration of p24 present in patients with high-titered antibodies to p24 were lower than in those with low-titered antibodies, independent of whether and how the samples were denatured (FIG. 3). Since heat denaturation is capable of releasing all IC-bound Ag, this finding represents a true difference in the amount of total Ag present at these different stages. This is in agreement with the results of other tests for virus that are not influenced by the titer of anti-HIV antibodies, such as the detection of virion genome by RNA-PCR. Testing with this method has indicated a lower average presence and concentration of virus at early stage of HIV infection (Zhang et al., *AIDS*, 5:675-681, 1991). It has been well established that the early stages of HIV infection are correlated with high-titered antibody to p24 (Schüpbach et al., *N. Engl. J. Med.*, 312:265–270, 1985; Lange et al., *Br. Med. J.*, 293:1489–1492, 1986; Weber et al., *Lancet*, i:119–122, 1987). It is assumed, therefore, that the sera shown in FIGS. 3B to D represent early stages while those in FIGS. 3E and F may represent late-stage infection. A different sample population has been tested by both heat-denatured Ag test and RNA-PCR and a good correlation of the two methods has been found.

Taken together, heat denaturation of sera (i) improves the early detection of antigenemia and (ii) permits the quantitative assessment of total antigen. The first will be of benefit in the selection of patients for early antiviral treatment intervention and the second represents an easily measurable endpoint parameter in the assessment of treatment success, particularly in patients in whom antigen was not previously detectable. In addition, heat denaturation is superior to all other described methods of IC disruption with respect to cost, ease of handling, and assay time. A further advantage is that HIV or other infectious agents are instantly rendered uninfectious. Finally, heat destruction of antibody binding function also destroys the IgG binding functions of rheumatoid factors and thus a possible cause of false-positive results.

Although the present investigations were restricted to the analysis of HIV Ag, they have a more general bearing: They show a simple way of solving the familiar problem of incomplete Ag detection in the presence of high-titered antibody. It is suggested that heat-denatured Ag be employed for the production of antibodies that will be used as capturing or tracing antibodies in Ag detection tests. Heat denaturation of samples before antigen testing will then become a standard procedure for antigen testing.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A method for the detection and quantitative determination of an antigen in a test sample containing immune complexes of the antigen bound to antibodies specific for the antigen and to rheumatoid factors, said method comprising:

a. heat-treating the sample at about neutral or physiological pH at a temperature of about 100° C. for 3 to 10 minutes, such that the antibodies present in the immune complexes no longer bind the antigen, thereby releasing the antigen from the immune complexes and eliminating interference with rheumatoid factors; and b. testing the heat-treated sample in an antigen assay which uses reagents which recognize the heat-treated antigen.

2. The method of claim 1, wherein the antigen is of an infectious agent.

3. The method of claim 2, wherein the antigen is a viral antigen.

4. The method of claim 3, wherein the antigen is an antigen of a human immunodeficiency virus (HIV).

5. The method of claim 3, wherein the antigen is an antigen of a human T-cell leukemia virus (HTLV).

6. The method of claim 3, wherein the antigen is an of a human hepatitis virus.

7. The method of claim 1, wherein the antigen is a bacterial antigen.

8. The method of claim 1, wherein the antigen is a fungal antigen.

9. The method of claim 1, wherein the antigen is a protozoan antigen.

10. The method of claim 1, wherein the heat-treating results in heat-denaturation of antigen in the test sample.

11. The method of claim 10, wherein reagents that recognize heat-denatured antigen are traced or captured.

* * * * *